United States Patent
Arnold et al.

(10) Patent No.: US 12,390,249 B2
(45) Date of Patent: Aug. 19, 2025

(54) ACCESS SHEATH WITH VALVE ASSEMBLY

(71) Applicant: Teleflex Life Sciences LLC, Wilmington, DE (US)

(72) Inventors: Donald Richard Arnold, Montrose, PA (US); Nathaniel Haim Maor, Chester Springs, PA (US)

(73) Assignee: Teleflex Life Sciences LLC, Wilmington, DE (US)

( * ) Notice: Subject to any disclaimer, the term of this patent is extended or adjusted under 35 U.S.C. 154(b) by 123 days.

(21) Appl. No.: 16/944,778

(22) Filed: Jul. 31, 2020

(65) Prior Publication Data

US 2022/0031353 A1    Feb. 3, 2022

(51) Int. Cl.
*A61B 17/34* (2006.01)

(52) U.S. Cl.
CPC ...... *A61B 17/3423* (2013.01); *A61B 17/3498* (2013.01)

(58) Field of Classification Search
CPC ............ A61B 17/3423; A61B 17/3498; A61B 2017/3464; A61M 2039/0626; A61M 2039/0633; A61M 2039/064; A61M 2039/0653; A61M 2039/066
See application file for complete search history.

(56) References Cited

U.S. PATENT DOCUMENTS

| | | | |
|---|---|---|---|
| 3,125,095 A | 3/1964 | Kaufman et al. | |
| 4,665,918 A | 5/1987 | Garza et al. | |
| 4,760,847 A | 8/1988 | Vaillancourt | |
| 4,798,594 A * | 1/1989 | Hillstead | A61M 39/0606 604/167.04 |
| 4,890,612 A | 1/1990 | Kensey | |
| 4,895,346 A * | 1/1990 | Steigerwald | F16K 7/20 604/167.04 |
| 4,895,565 A | 1/1990 | Hillstead | |
| 4,990,151 A | 2/1991 | Wallsten | |
| 5,021,059 A | 6/1991 | Kensey et al. | |

(Continued)

FOREIGN PATENT DOCUMENTS

| | | |
|---|---|---|
| EP | 0474752 B1 | 6/1995 |
| EP | 0766947 A2 | 4/1997 |

(Continued)

OTHER PUBLICATIONS

PCT International Search Report mailed Oct. 22, 2021 in PCT/US2021/041730.

(Continued)

*Primary Examiner* — Tracy L Kamikawa
(74) *Attorney, Agent, or Firm* — Dorsey & Whitney LLP

(57) ABSTRACT

An access sheath and method of assembling the access sheath. The access sheath includes a hub, a cartridge carried by the hub, the cartridge having a first valve, a second valve spaced from the first valve along a central axis, and a spacer disposed between the first valve and the second valve, wherein the first valve and the second valve each have at least two slits that extend along, and twist about, the central axis, and a shaft assembly having a shaft hub and a shaft that extends from the shaft hub in the distal direction. The access sheath provides a liquid-tight seal when receiving the introducer and other devices to prevent leakage and blood loss and to decrease device insertion forces.

35 Claims, 13 Drawing Sheets

(56) References Cited

U.S. PATENT DOCUMENTS

| | | | |
|---|---|---|---|
| 5,026,377 A | 6/1991 | Burton et al. | |
| 5,041,095 A | 8/1991 | Littrell | |
| 5,059,183 A | 10/1991 | Semrad | |
| 5,222,974 A | 6/1993 | Kensey et al. | |
| 5,282,827 A | 2/1994 | Kensey et al. | |
| 5,292,309 A | 3/1994 | Tassel et al. | |
| 5,306,254 A | 4/1994 | Nash et al. | |
| 5,322,508 A | 6/1994 | Viera | |
| 5,324,306 A | 6/1994 | Makower et al. | |
| 5,360,414 A | 11/1994 | Yarger | |
| 5,363,847 A | 11/1994 | Viera | |
| 5,411,520 A | 5/1995 | Nash et al. | |
| 5,531,759 A | 7/1996 | Kensey et al. | |
| 5,545,178 A * | 8/1996 | Kensey | A61B 17/0057 606/232 |
| 5,643,318 A | 7/1997 | Tsukernik et al. | |
| 5,662,681 A | 9/1997 | Nash et al. | |
| 5,700,277 A | 12/1997 | Nash et al. | |
| 5,702,421 A | 12/1997 | Schneidt | |
| 5,843,124 A | 12/1998 | Hammerslag | |
| 6,010,520 A | 1/2000 | Pattison | |
| 6,056,768 A | 5/2000 | Cates et al. | |
| 6,090,130 A | 7/2000 | Nash et al. | |
| 6,107,004 A | 8/2000 | Donadio, III | |
| 6,179,863 B1 | 1/2001 | Kensey et al. | |
| 6,245,054 B1 | 6/2001 | Fuimaono et al. | |
| 6,425,911 B1 | 7/2002 | Akerfeldt et al. | |
| 6,440,151 B1 | 8/2002 | Cragg et al. | |
| 6,440,153 B2 | 8/2002 | Cragg et al. | |
| 6,447,534 B2 | 9/2002 | Cragg et al. | |
| 6,494,848 B1 | 12/2002 | Sommercorn et al. | |
| 6,682,489 B2 * | 1/2004 | Tenerz | A61B 17/0057 606/213 |
| 6,860,895 B1 | 3/2005 | Akerfeldt et al. | |
| 7,037,322 B1 | 5/2006 | Sing et al. | |
| 7,044,916 B2 | 5/2006 | Tenerz et al. | |
| 7,073,509 B2 | 7/2006 | Tenerz et al. | |
| 7,094,209 B2 | 8/2006 | Egnelöv et al. | |
| 7,285,097 B2 | 10/2007 | Tenerz et al. | |
| 7,316,704 B2 | 1/2008 | Bagaoisan et al. | |
| 7,597,705 B2 | 10/2009 | Forsberg et al. | |
| 7,618,436 B2 | 11/2009 | Forsberg | |
| 7,648,493 B2 | 1/2010 | Forsberg et al. | |
| 7,695,493 B2 | 4/2010 | Saadat et al. | |
| 7,850,654 B2 | 12/2010 | Belhe et al. | |
| 7,905,902 B2 | 3/2011 | Huitema et al. | |
| 8,002,749 B2 * | 8/2011 | Macatangay | A61M 39/0613 604/167.03 |
| 8,029,533 B2 | 10/2011 | Bagaoisan et al. | |
| 8,097,007 B2 | 1/2012 | Evans et al. | |
| 8,137,321 B2 * | 3/2012 | Argentine | A61M 25/0097 604/167.06 |
| 8,273,094 B2 | 9/2012 | Belhe et al. | |
| 8,337,522 B2 | 12/2012 | Ditter | |
| 8,382,793 B2 | 2/2013 | Egnelöv et al. | |
| 8,435,256 B2 | 5/2013 | Lehe et al. | |
| 8,444,673 B2 | 5/2013 | Thielen et al. | |
| 8,540,750 B2 | 9/2013 | Tegels | |
| 8,685,059 B2 | 4/2014 | Walters | |
| 8,870,917 B2 | 10/2014 | Walters | |
| 8,926,564 B2 * | 1/2015 | King | A61M 25/0668 604/167.03 |
| 8,974,476 B2 | 3/2015 | Tegels | |
| 9,089,363 B2 * | 7/2015 | Dooney, Jr. | A61B 17/3423 |
| 9,675,371 B2 | 6/2017 | Shimon | |
| 9,757,104 B2 | 9/2017 | Walters et al. | |
| 10,154,835 B2 | 12/2018 | Walters et al. | |
| 10,383,611 B2 | 8/2019 | Walters et al. | |
| 10,390,810 B2 | 8/2019 | Walters et al. | |
| 10,448,937 B2 | 10/2019 | Walters et al. | |
| 10,485,524 B2 | 11/2019 | Walters et al. | |
| 10,555,727 B2 | 2/2020 | Walters et al. | |
| 10,639,019 B2 | 5/2020 | Walters | |
| 10,668,253 B2 | 6/2020 | Jacobs | |
| 10,682,128 B2 | 6/2020 | Walters et al. | |
| 11,020,224 B2 | 6/2021 | Jacobs | |
| 11,123,053 B2 | 9/2021 | Walters et al. | |
| 11,419,592 B2 | 8/2022 | Walters et al. | |
| 11,576,663 B2 | 2/2023 | Walters et al. | |
| 11,589,855 B2 | 2/2023 | Walters et al. | |
| 11,779,320 B2 | 10/2023 | Walters et al. | |
| 2001/0003158 A1 | 6/2001 | Kensey et al. | |
| 2001/0044639 A1 | 11/2001 | Levinson | |
| 2002/0022822 A1 | 2/2002 | Cragg et al. | |
| 2003/0078616 A1 | 4/2003 | Ginn et al. | |
| 2004/0138674 A1 | 7/2004 | Egnelov et al. | |
| 2004/0147950 A1 | 7/2004 | Mueller et al. | |
| 2004/0204741 A1 | 10/2004 | Egnelov et al. | |
| 2004/0267308 A1 | 12/2004 | Bagaoisan et al. | |
| 2005/0085856 A1 | 4/2005 | Ginn | |
| 2005/0107820 A1 | 5/2005 | Forsberg et al. | |
| 2005/0107826 A1 | 5/2005 | Zhu et al. | |
| 2005/0107827 A1 | 5/2005 | Paprocki | |
| 2005/0125030 A1 | 6/2005 | Forsberg et al. | |
| 2005/0277961 A1 | 12/2005 | Stone et al. | |
| 2006/0058844 A1 | 3/2006 | White et al. | |
| 2006/0217664 A1 | 9/2006 | Hattler et al. | |
| 2006/0229673 A1 | 10/2006 | Forsberg | |
| 2007/0123936 A1 | 5/2007 | Goldin et al. | |
| 2007/0282373 A1 | 12/2007 | Ashby et al. | |
| 2008/0082123 A1 | 4/2008 | Forsberg et al. | |
| 2008/0157017 A1 | 7/2008 | Macatangay et al. | |
| 2008/0306509 A1 | 12/2008 | Osborne | |
| 2009/0054926 A1 | 2/2009 | Pipenhagen et al. | |
| 2009/0088793 A1 | 4/2009 | Bagaoisan et al. | |
| 2009/0099598 A1 | 4/2009 | McDevitt et al. | |
| 2009/0137870 A1 | 5/2009 | Bakos et al. | |
| 2009/0171387 A1 | 7/2009 | Pipenhagen et al. | |
| 2009/0248064 A1 | 10/2009 | Preinitz | |
| 2009/0312790 A1 | 12/2009 | Forsberg et al. | |
| 2009/0318894 A1 | 12/2009 | Lafitte et al. | |
| 2010/0016887 A1 | 1/2010 | Inderbitzi | |
| 2010/0168789 A1 | 7/2010 | Bagaoisan et al. | |
| 2010/0179589 A1 | 7/2010 | Roorda et al. | |
| 2010/0185216 A1 | 7/2010 | Garrison et al. | |
| 2011/0004162 A1 | 1/2011 | Tal | |
| 2011/0046665 A1 | 2/2011 | Green et al. | |
| 2011/0054456 A1 | 3/2011 | Thompson et al. | |
| 2011/0160765 A1 | 6/2011 | Melmed et al. | |
| 2011/0208222 A1 | 8/2011 | Ljahnicky et al. | |
| 2011/0213414 A1 | 9/2011 | McGuckin, Jr. et al. | |
| 2011/0213415 A1 | 9/2011 | McGuckin, Jr. et al. | |
| 2011/0301619 A1 | 12/2011 | Walters | |
| 2012/0010634 A1 | 1/2012 | Crabb et al. | |
| 2012/0022585 A1 | 1/2012 | Atanasoska et al. | |
| 2012/0065668 A1 | 3/2012 | Ginn et al. | |
| 2012/0071079 A1 | 3/2012 | Pipenhagen et al. | |
| 2012/0083829 A1 | 4/2012 | Ginn et al. | |
| 2012/0101525 A1 | 4/2012 | Jenson et al. | |
| 2012/0109192 A1 | 5/2012 | Egneloev et al. | |
| 2012/0116446 A1 | 5/2012 | Green et al. | |
| 2012/0143244 A1 | 6/2012 | Hill et al. | |
| 2012/0143245 A1 | 6/2012 | Tegels | |
| 2012/0143249 A1 | 6/2012 | Jenson et al. | |
| 2012/0158044 A1 | 6/2012 | Jenson et al. | |
| 2012/0165854 A1 | 6/2012 | Pipenhagen et al. | |
| 2012/0245517 A1 | 9/2012 | Tegels | |
| 2012/0245597 A1 | 9/2012 | Tegels | |
| 2012/0245624 A1 | 9/2012 | Glazier et al. | |
| 2012/0283770 A1 | 11/2012 | Kramer et al. | |
| 2012/0296275 A1 | 11/2012 | Martin et al. | |
| 2013/0006297 A1 | 1/2013 | Drasler | |
| 2013/0006298 A1 | 1/2013 | Terwey | |
| 2013/0025588 A1 | 1/2013 | Bosel | |
| 2013/0035719 A1 | 2/2013 | Hill et al. | |
| 2013/0072949 A1 | 3/2013 | Halac et al. | |
| 2013/0079802 A1 | 3/2013 | Halac et al. | |
| 2013/0103077 A1 | 4/2013 | Ditter et al. | |
| 2013/0131718 A1 | 5/2013 | Jenson et al. | |
| 2013/0144316 A1 | 6/2013 | Mccrea et al. | |
| 2013/0150884 A1 | 6/2013 | Belhe et al. | |
| 2013/0178895 A1 | 7/2013 | Walters et al. | |
| 2013/0226227 A1 | 8/2013 | Terwey | |

(56) References Cited

U.S. PATENT DOCUMENTS

| | | |
|---|---|---|
| 2014/0039264 A1 | 2/2014 | Heiman |
| 2014/0046217 A1 | 2/2014 | Lim et al. |
| 2014/0046220 A1 | 2/2014 | Nelson et al. |
| 2014/0094846 A1 | 4/2014 | Lim et al. |
| 2014/0188160 A1 | 7/2014 | Tegels et al. |
| 2014/0200611 A1 | 7/2014 | Walters |
| 2014/0222064 A1 | 8/2014 | Tegels |
| 2014/0236088 A1 | 8/2014 | Al-Rashdan et al. |
| 2014/0309686 A1 | 10/2014 | Ginn et al. |
| 2014/0364899 A1 | 12/2014 | Ginn et al. |
| 2015/0068009 A1 | 3/2015 | Walters |
| 2015/0100083 A1 | 4/2015 | Walters et al. |
| 2015/0173794 A1 | 6/2015 | Kurth et al. |
| 2016/0228109 A1 | 8/2016 | Jacobs et al. |
| 2017/0135725 A1 | 5/2017 | Tegels |
| 2017/0333015 A1 | 11/2017 | Walters et al. |
| 2019/0015204 A1 | 1/2019 | Jacobs |
| 2019/0015637 A1 | 1/2019 | Jacobs |
| 2019/0110781 A1 | 4/2019 | Walters et al. |
| 2019/0336116 A1 | 11/2019 | Walters et al. |
| 2020/0000448 A1 | 1/2020 | Walters et al. |
| 2020/0146661 A1 | 5/2020 | Walters et al. |
| 2020/0289101 A1 | 9/2020 | Walters |
| 2022/0273277 A1 | 9/2022 | Walters et al. |
| 2022/0338852 A1 | 10/2022 | Walters |
| 2024/0325011 A1 | 10/2024 | Walters et al. |

FOREIGN PATENT DOCUMENTS

| | | |
|---|---|---|
| EP | 0797953 A2 | 10/1997 |
| EP | 1163020 A1 | 12/2001 |
| EP | 1169968 A1 | 1/2002 |
| EP | 1222896 A2 | 7/2002 |
| EP | 1254634 A1 | 11/2002 |
| EP | 0664687 B2 | 8/2003 |
| EP | 1371333 A1 | 12/2003 |
| EP | 1413255 A1 | 4/2004 |
| EP | 1440661 A1 | 7/2004 |
| EP | 1532929 A1 | 5/2005 |
| EP | 1658811 A1 | 5/2006 |
| EP | 1695667 A1 | 8/2006 |
| EP | 1836967 A1 | 9/2007 |
| EP | 1836968 A1 | 9/2007 |
| EP | 2055236 A1 | 5/2009 |
| EP | 2064999 A2 | 6/2009 |
| EP | 2213247 A1 | 8/2010 |
| EP | 2215974 A2 | 8/2010 |
| EP | 1919367 B1 | 10/2011 |
| EP | 1874195 B1 | 1/2012 |
| EP | 1893100 B1 | 3/2012 |
| EP | 2227148 B1 | 4/2012 |
| EP | 1893099 B1 | 6/2012 |
| EP | 1893098 B1 | 1/2014 |
| EP | 2611366 B1 | 7/2014 |
| EP | 2605707 B1 | 10/2014 |
| EP | 1773438 B1 | 1/2017 |
| WO | 1989011301 A1 | 11/1989 |
| WO | 1990014796 A1 | 12/1990 |
| WO | 1992014396 A1 | 9/1992 |
| WO | 1993008743 A1 | 5/1993 |
| WO | 1993008746 A3 | 8/1993 |
| WO | 1994007421 A1 | 4/1994 |
| WO | 1998005259 A1 | 2/1998 |
| WO | 1999022646 A1 | 5/1999 |
| WO | 2000078226 A1 | 12/2000 |
| WO | 2003094740 A1 | 11/2003 |
| WO | 2004096056 A2 | 11/2004 |
| WO | 2005002451 A1 | 1/2005 |
| WO | 2005039387 A2 | 5/2005 |
| WO | 2005060514 A2 | 7/2005 |
| WO | 2006075228 A1 | 7/2006 |
| WO | 2006110615 A2 | 10/2006 |
| WO | 2007035187 A2 | 3/2007 |
| WO | 2008036634 A1 | 3/2008 |
| WO | 2009005722 A1 | 1/2009 |
| WO | 2009025836 A1 | 2/2009 |
| WO | 2009029914 A1 | 3/2009 |
| WO | 2009035921 A2 | 3/2009 |
| WO | 2009088440 A1 | 7/2009 |
| WO | 2009088441 A1 | 7/2009 |
| WO | 2009112930 A2 | 9/2009 |
| WO | 2010129042 A1 | 11/2010 |
| WO | 2011014244 A1 | 2/2011 |
| WO | 2011019374 A1 | 2/2011 |
| WO | 2011025529 A1 | 3/2011 |
| WO | 2011025543 A2 | 3/2011 |
| WO | 2011037635 A1 | 3/2011 |
| WO | 2011146729 A2 | 11/2011 |
| WO | 2011156498 A1 | 12/2011 |
| WO | 2012009007 A1 | 1/2012 |
| WO | 2012012641 A1 | 1/2012 |
| WO | 2012045356 A1 | 4/2012 |
| WO | 2012061486 A2 | 5/2012 |
| WO | 2012064888 A2 | 5/2012 |
| WO | 2012083045 A1 | 6/2012 |
| WO | 2012145356 A1 | 10/2012 |
| WO | 2012145362 A1 | 10/2012 |
| WO | 2012148745 A1 | 11/2012 |
| WO | 2012148747 A1 | 11/2012 |
| WO | 2012158662 A1 | 11/2012 |
| WO | 2012158737 A1 | 11/2012 |
| WO | 2012158738 A1 | 11/2012 |
| WO | 2012158740 A1 | 11/2012 |
| WO | 2012158931 A1 | 11/2012 |
| WO | 2013063227 A1 | 5/2013 |
| WO | 2013081659 A1 | 6/2013 |
| WO | 2014150154 A1 | 9/2014 |
| WO | 2015099977 A1 | 7/2015 |
| WO | 2017123853 A1 | 7/2017 |

OTHER PUBLICATIONS

PCT Written Opinion mailed Oct. 22, 2021 in PCT/US2021/041730.
Extended European Search Report and Opinion mailed Jun. 16, 2021 in EP Application No. 21163623.8.
International Search Report and Written Opinion for International Application No. PCT/US2012/061855 dated Jan. 22, 2013 (21 pages).
Koh, Wui-Jin et al. "Femoral vessel depth and the implications for groin node radiation," 1993, International Journal of Radiation Oncology 'Biology' Physics, vol. 27, p. 969-974.
Officer Gunter Held, International Search Report and the Written Opinion, International Patent Application PCT/US2017/013314, dated Apr. 18, 2017, 11 pp.
PCT International Preliminary Report on Patentability, PCT/US2014/068694, Jun. 28, 2016, 11 pp.
PCT International Search Report and the Written Opinion, PCT/US2014/068694, Mar. 17, 2015, 17 pp.
Badawi et al, "A Simple Percutaneous Technique for Hemostasis and Closure after Transcatheter Aortic Valve Implantation", Catheterization and Cardiovascular Interventions, Jan. 1, 2012, 79(1), 152-155.
Bui et al, "Double-Wire Angio-Seal Closure Technique after Balloon Aortic Valvuloplasty", Catheterization and Cardiovascular Interventions, 2010, 75, 488-492.
Extended European Search Report mailed Sep. 6, 2021 in EP Application No. 21166157.4.
European Search Report and Search Opinion mailed May 10, 2023, in EP Patent Application No. 23153276.3.
Extended European Search Report and Opinion mailed Jul. 24, 2024 in EP Application No. 24160990.8.

* cited by examiner

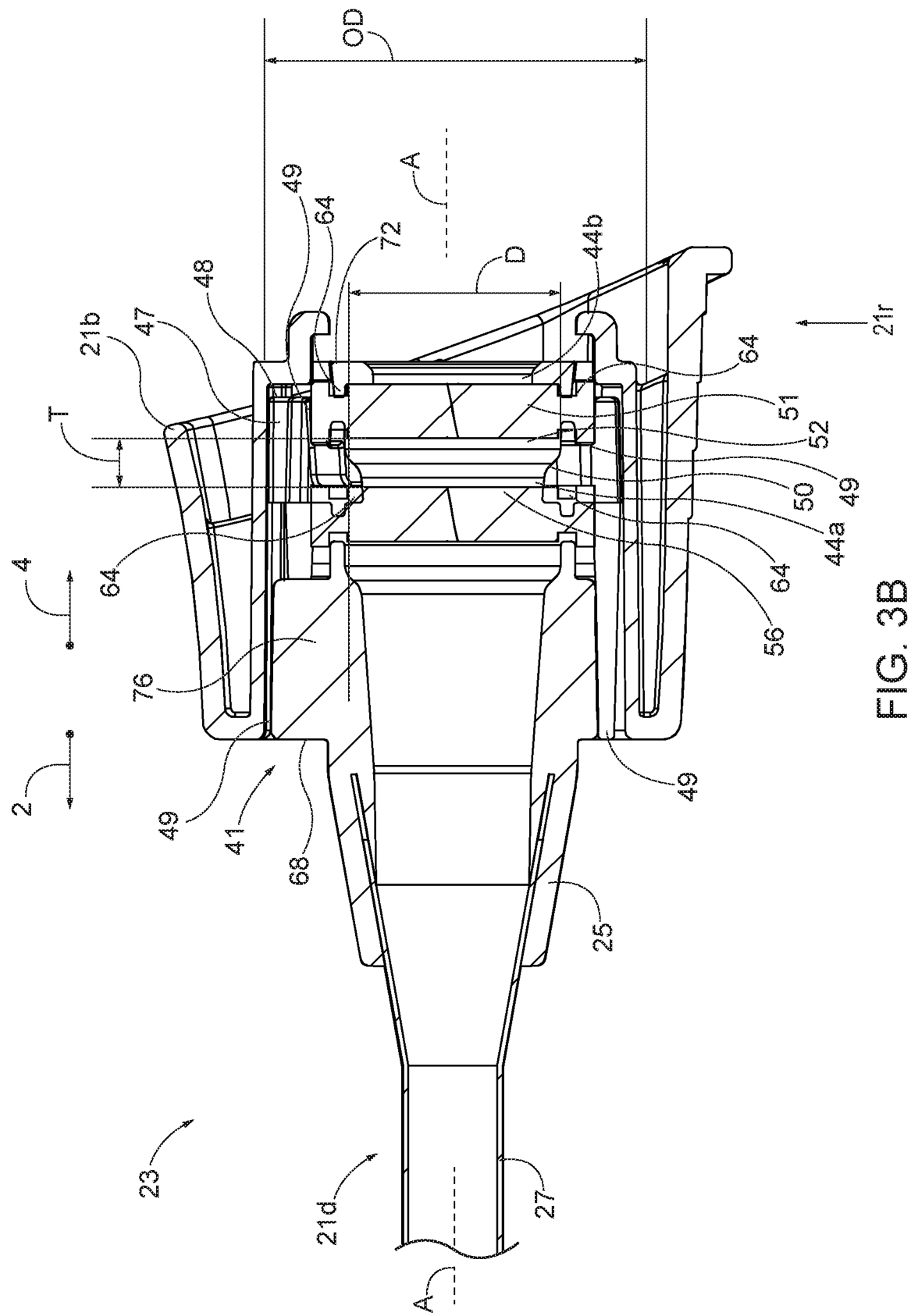

ACCESS SHEATH WITH VALVE ASSEMBLY

TECHNICAL FIELD

The present disclosure relates to an access sheath for device introduction and exchange in a vessel.

BACKGROUND

Percutaneous procedures often involve accessing vasculature with elongated instruments, e.g., catheters, deployed in an ordered sequence. During an interventional cardiovascular procedure access to the cardiovascular system may be obtained via an artery or vein in situations where an artery is not a suitable approach path. In one example, a vascular closure system may include a sheath introducer and a delivery system having a sealing unit designed to seal a puncture in a vessel. Such systems and related devices may function to exchange a procedure access sheath used to guide a catheter (or other medical device) into the vessel, e.g. the femoral artery or the aorta, with an access sheath for use with a device. The access sheath may have a valve that is designed to minimize blood loss during device insertion into the access sheath. Current valves, however, present leakage issues as well as high device introduction forces. In order to accommodate larger diameters, the valves stretch beyond their tear limits. The tear reduces the likelihood of the valve being able to seal around a guidewire prior to introduction of the delivery system or during catheter exchange. Leakage may occur during the exchange between catheters, such as between the sheath introducer and the delivery system, resulting in blood loss. In addition, existing efforts to improve leakage can increase insertion forces, as the delivery system requires more force to pierce through the valve.

SUMMARY

An embodiment of the present disclosure is an access sheath configured to be disposed along a guidewire into a puncture of a vessel. The access sheath includes a hub having a proximal end and a distal end spaced from the proximal end. The access sheath further includes a cartridge carried by the hub, the cartridge having a first valve, a second valve spaced from the first valve along central axis, and a spacer disposed between the first valve and the second valve. The first valve and the second valve each have at least two slits that extend through first valve and the second valve, respectively, along the central axis. The access sheath further includes a shaft assembly having a shaft hub coupled to hub disposed relative the cartridge in a distal direction along the central axis, and a shaft that extends from the shaft hub in the distal direction.

Another embodiment of the present disclosure is an access sheath. The access sheath is configured to be disposed along a guidewire into a puncture of a vessel. The access sheath includes a hub having a proximal end and a distal end spaced from the proximal end. The access sheath further includes a cartridge carried by the hub. The cartridge has a first valve, a second valve spaced from the first valve along a central axis, and a spacer disposed between the first valve and the second valve. The first valve and the second valve each have at least two slits that extend along, and twist about, the central axis. The access sheath further includes a shaft assembly having a shaft hub coupled to the hub and disposed relative to the cartridge in a distal direction along the central axis, and a shaft that extends from the shaft hub in the distal direction.

A further embodiment of the present disclosure is a vascular closure system. The vascular closure system includes an access sheath configured to be inserted into the vessel. The access sheath has a proximal end and a distal end spaced from the proximal end along a central axis. The access sheath further includes a hub, a cartridge carried by the hub, the cartridge having a first valve, a second valve spaced from the first valve along the central axis, and a spacer disposed between the first valve and the second valve. The first valve and the second valve each have at least two slits that extend along the central axis. The access sheath further includes a shaft assembly having a shaft hub coupled to hub and disposed relative to the cartridge in a distal direction along the central axis, and a shaft that extends from the shaft hub in the distal direction to define the distal end of the access sheath. The access sheath further includes an access channel that extends from the proximal end at the hub to the distal end along the central axis. The vascular closure system further includes a deployment assembly having a sealing element configured to seal the puncture in the vessel. The deployment assembly is insertable into the access channel and into engagement with the first valve and the second valve such that the first valve and second valve stretch around the deployment assembly.

Another embodiment of the present disclosure is a method. The method includes placing a first valve inside a sheath hub of a shaft assembly, the shaft assembly including an elongated shaft that extends from the sheath hub. The method further includes coupling the sheath hub to a cartridge with a tool. The method further includes placing a second valve in the cartridge adjacent a spacer such that second valve is spaced apart and aligned with the first valve, wherein the first valve and the second valve each have at least two slits. The method further includes inserting an assembly of the cartridge and sheath hub to a hub to form an access sheath.

BRIEF DESCRIPTION OF THE DRAWINGS

The foregoing summary, as well as the following detailed description, will be better understood when read in conjunction with the appended drawings. The drawings show illustrative embodiments of the disclosure. It should be understood, however, that the application is not limited to the precise arrangements and instrumentalities shown.

FIG. 3B is a side sectional view of the access sheath shown in FIG. 3A;

DETAILED DESCRIPTION OF ILLUSTRATIVE EMBODIMENTS

Figure 1:
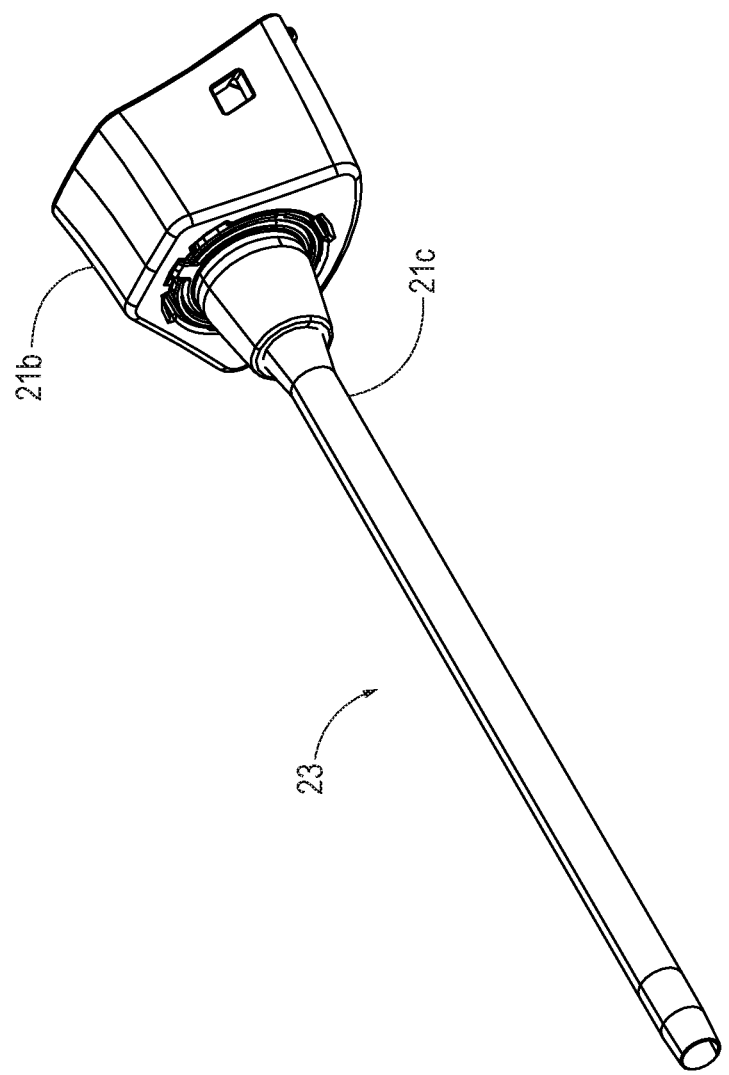
FIG. 1 is a perspective view of an access sheath according to an embodiment of the present disclosure.

Certain terminology is used in the following description for convenience only and is not limiting. The words "right", "left", "lower" and "upper" designate directions in the drawings to which reference is made. The words "proximally" and "distally" refer to directions toward and away from, respectively, the individual operating the system. The terminology includes the above-listed words, derivatives thereof and words of similar import.

Figure 2:
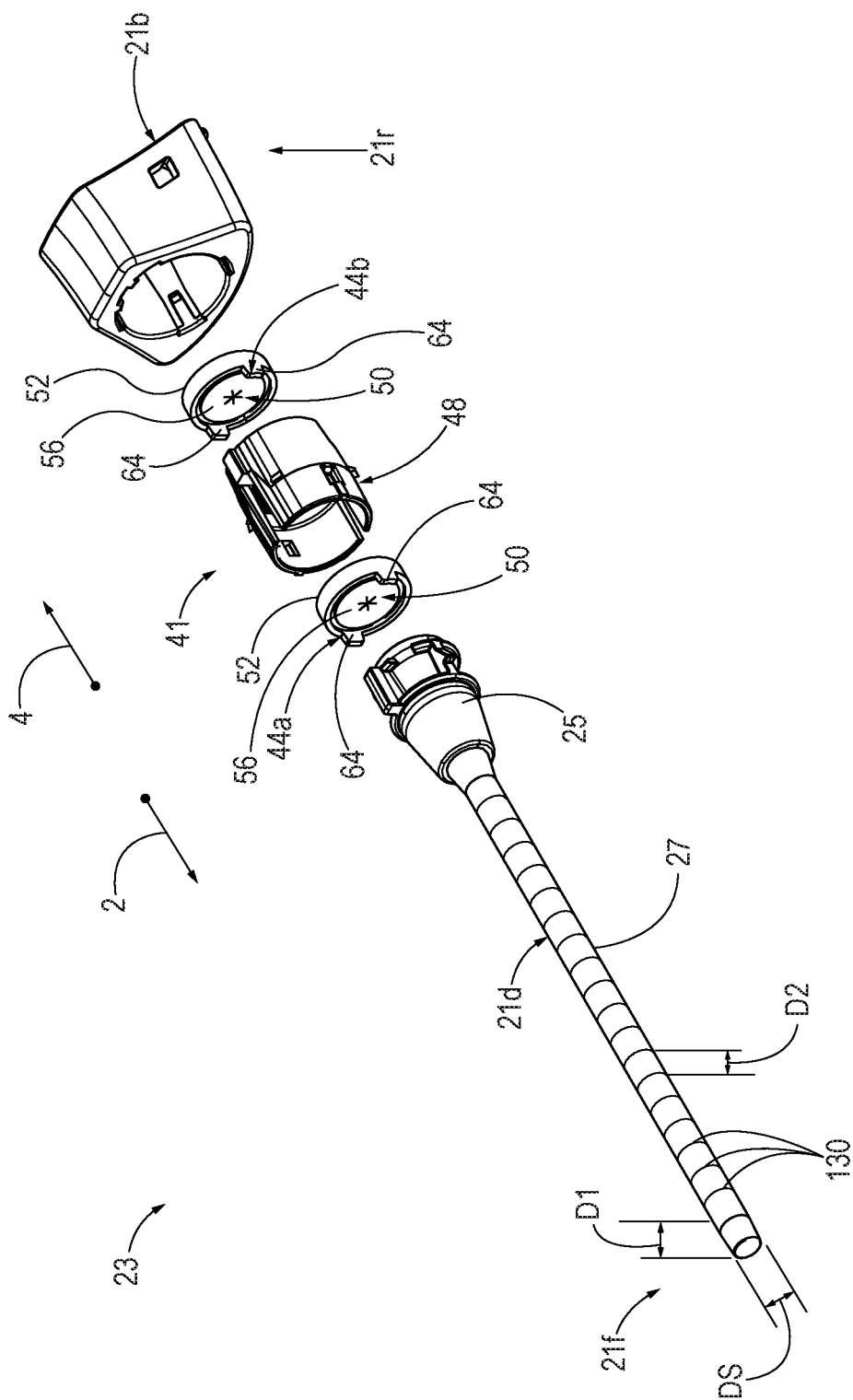
FIG. 2 is an exploded view of the access sheath shown in FIG. 1.

Referring to FIGS. 1 and 2, an access sheath 23 is configured to be inserted into a vessel of a patient for sheath introduction or exchange in a vessel. The access sheath 23 has a front end 21f, a rear end 21r opposite to the front end 21f, and a lumen (not numbered) that extends from the front end 21f to the rear end 21r. The access sheath 23 includes a hub 21b, a shaft assembly 21d that extends from the hub 21b in the distal direction 2, and a valve assembly 41. The rear end 21r of the access sheath includes the hub 21b that is configured to be coupled to the deployment assembly 14 during a closure procedure. The shaft assembly 21d includes a shaft hub 25 coupled to the valve assembly 41 and a shaft 27 that extends from the shaft hub 25 in the distal direction 2. When the access sheath 23 is coupled to the deployment assembly 14, the shaft assembly 21d extends along the release component 22 and delivery component 26 in the distal direction 2. The shaft 27 includes at least one marker 130. Thus, there may be a single marker 130 or a plurality of markers 130. In the illustrated embodiment, the markers 130 are evenly spaced along the shaft 27 and can be positioned to aid in identifying the location of the shaft assembly 21d in the vessel. The marker 130 is one of a laser etch, radio opaque band, a radio opaque ink, or a radio opaque paint. The shaft 27 includes an outer diameter DS. In one embodiment, the outer diameter DS of the shaft 27 may be 14 F. In another embodiment, the outer diameter of the shaft may be 18 F. Other sizes are contemplated. In one example, the shaft length may vary as needed.

Figure 3A:
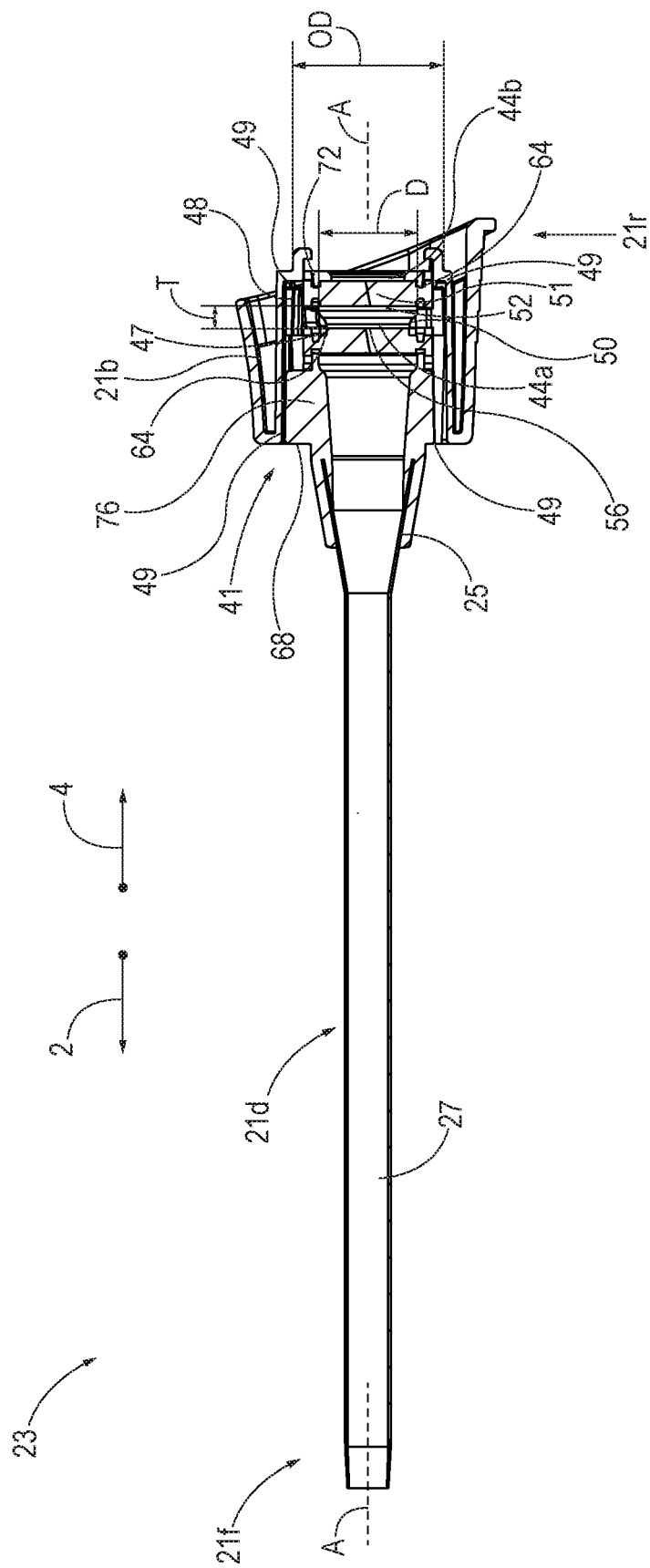
FIG. 3A is a side sectional view of the access sheath shown in FIGS. 1 and 2.

Referring to FIGS. 3A and 3B, the valve assembly 41 carries the valves 44a, 44b. As shown, the valve assembly 41 is coupled to the shaft assembly 21d and the hub 21b. The valve assembly 41 includes a cartridge 48 that carries a first valve 44a and a second valve 44b. The first and second valves 44a, 44b may be hemostasis valves and are configured to minimize the loss of blood during insertion of the deployment assembly 14 into the access sheath 23.

The cartridge 48 includes a cartridge body 47 that is configured to house and hold the first and second valves 44a, 44b. As shown the cartridge body 47 has a first end 68 and a second end 72 opposite the first end along the central axis A. The cartridge body 47 has an outer diameter OD that extends through and intersects the central axis A. The cartridge body 47 further defines an internal surface 76, which in turn, defines a spacer 51 that extends inwardly toward the central axis A. The spacer 51 is configured to separate the first valve 44a and the second valve 44b. The cartridge body 47 further defines one or more grooves 49 disposed on either end of the cartridge 48. In the illustrated embodiment, the cartridge 48 has an outer diameter of approximately 19 mm. The outer diameter OD can range between 15 mm and 30 mm as needed. The cartridge 48 may be formed from any polymeric material. It should be appreciated, however, that the cartridge 48 can be made of other materials and can have other configurations.

The first and second valves 44a, 44b include a body 50 having a proximal surface 52 and a distal surface 56 opposite the proximal surface 52 along the central axis A. The valve body 50 can further define a thickness T that extends from the proximal surface 52 to the distal surface 56 in a direction that is parallel to the central axis A. In the illustrated embodiment, the thickness of the first and second valves 44a, 44b is approximately 3 mm. However, the thickness T may range between 2 mm and 5 mm or higher as needed. Furthermore, each valve body has a circular cross-sectional shape to fit with the cartridge. As shown, each valve has a diameter D that intersects and is perpendicular to the central axis A. In one example, the diameter D of the first and second valves 44a, 44b is approximately 15 mm. The diameter D may range between 8 mm and 20 mm, as needed. This size permits the deployment assembly 14 to pass through the slits as explained further below. The first and second valves 44a, 44b may be made of silicone. It should be appreciated, however, that the first and second valves 44a, 44b can be made of other materials and can have other configurations.

The first and second valves 44a includes a set of tabs 64 disposed on the distal surface 56 of the body 50. The tabs 64 of the first valve 44a are configured to couple the first valve 44a to the shaft hub 25 of the shaft assembly 21d via the cartridge 48. The tabs 64 of the second valve 44b are configured to couple the second valve 44b to the hub 21b via the cartridge 48. The grooves 49 of the cartridge 48 with the tabs 64 of the first and second valves 44a, 44b, couple the first and second valves 44a, 44b to the shaft assembly 21d and hub 21b, respectively. This configuration further enhances sealing within the access sheath 23.

Figure 4A:
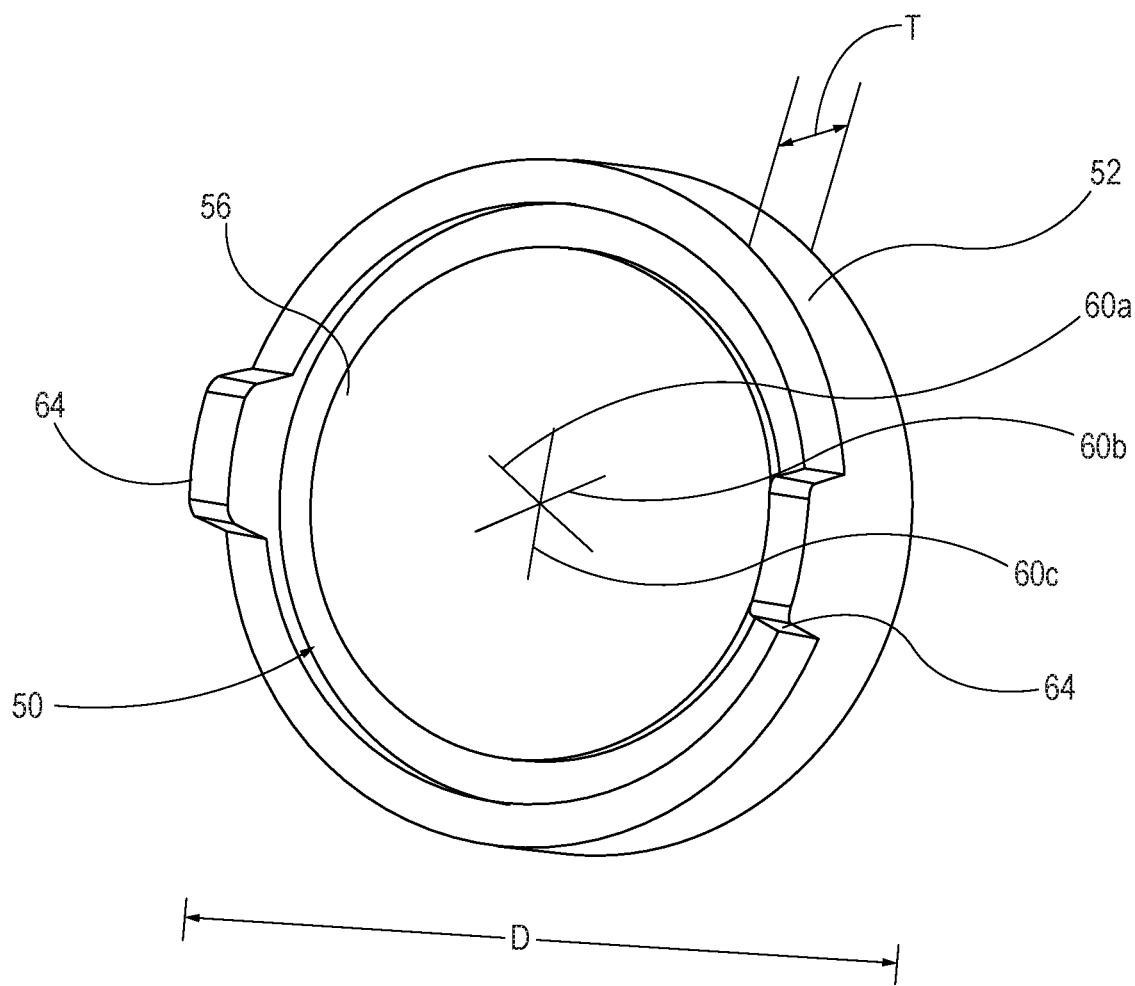
FIG. 4A is a perspective view of the valve shown in FIG. 2.
Figure 4B:
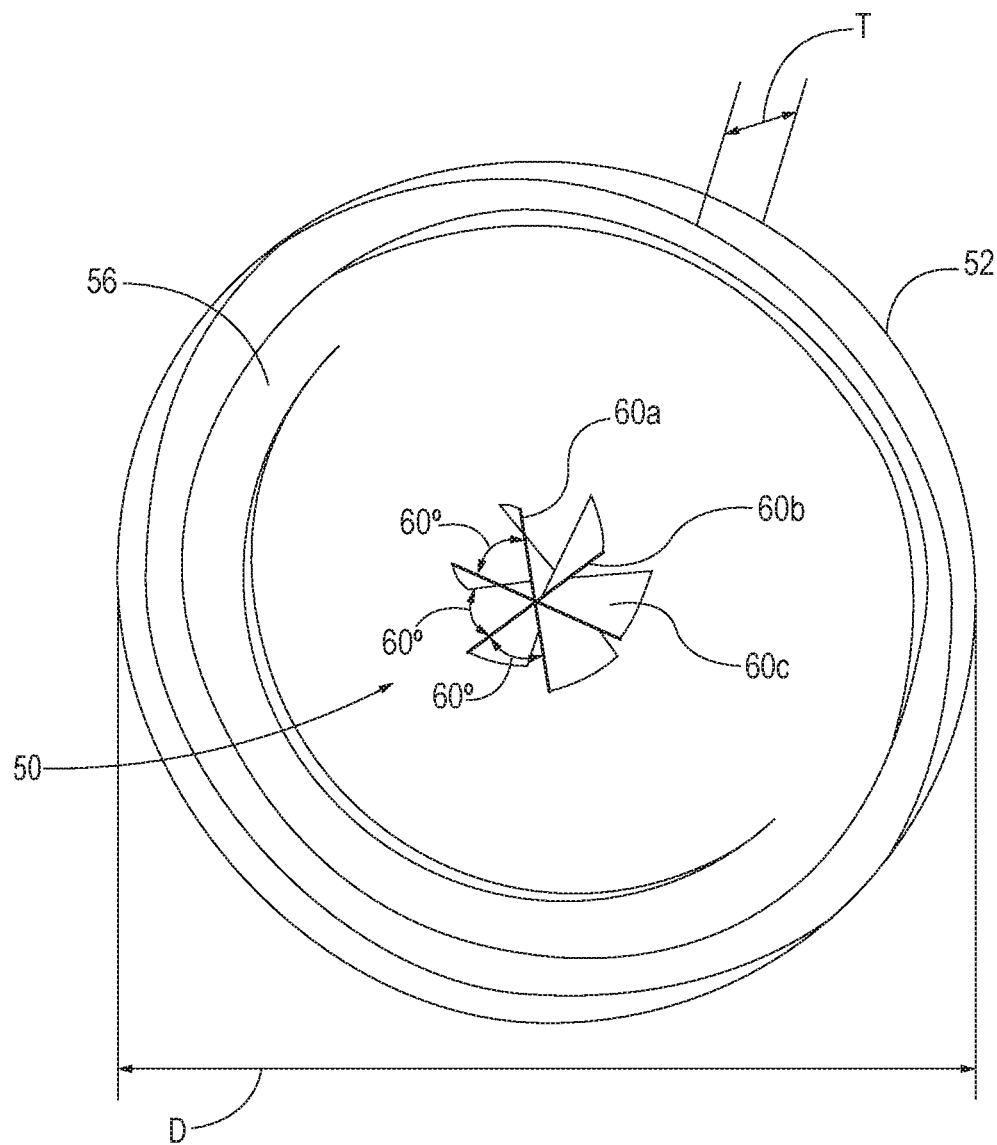
FIG. 4B is a perspective cross-sectional view of the valve shown in FIG. 4A.
Figure 5:
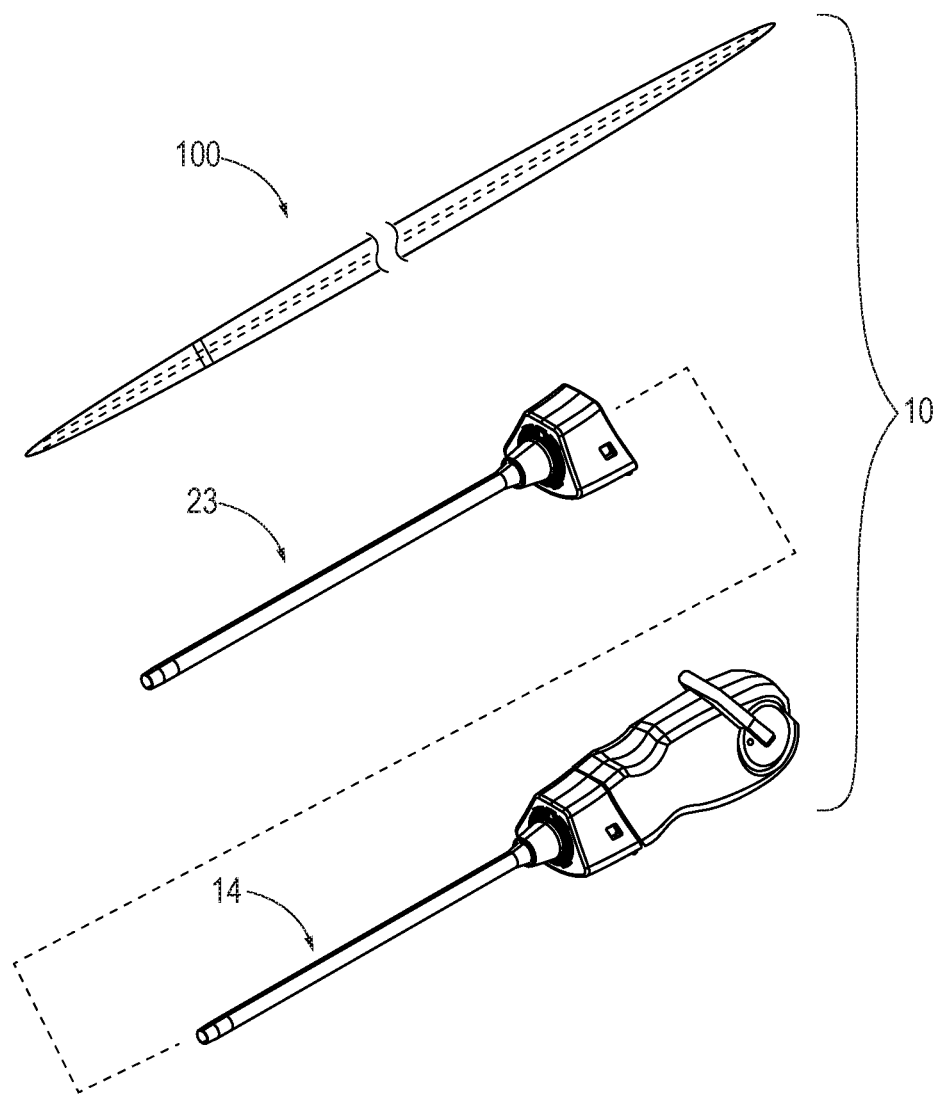
FIG. 5 is a perspective view of a vascular closure system according to an embodiment of the present disclosure.
Figure 6A:
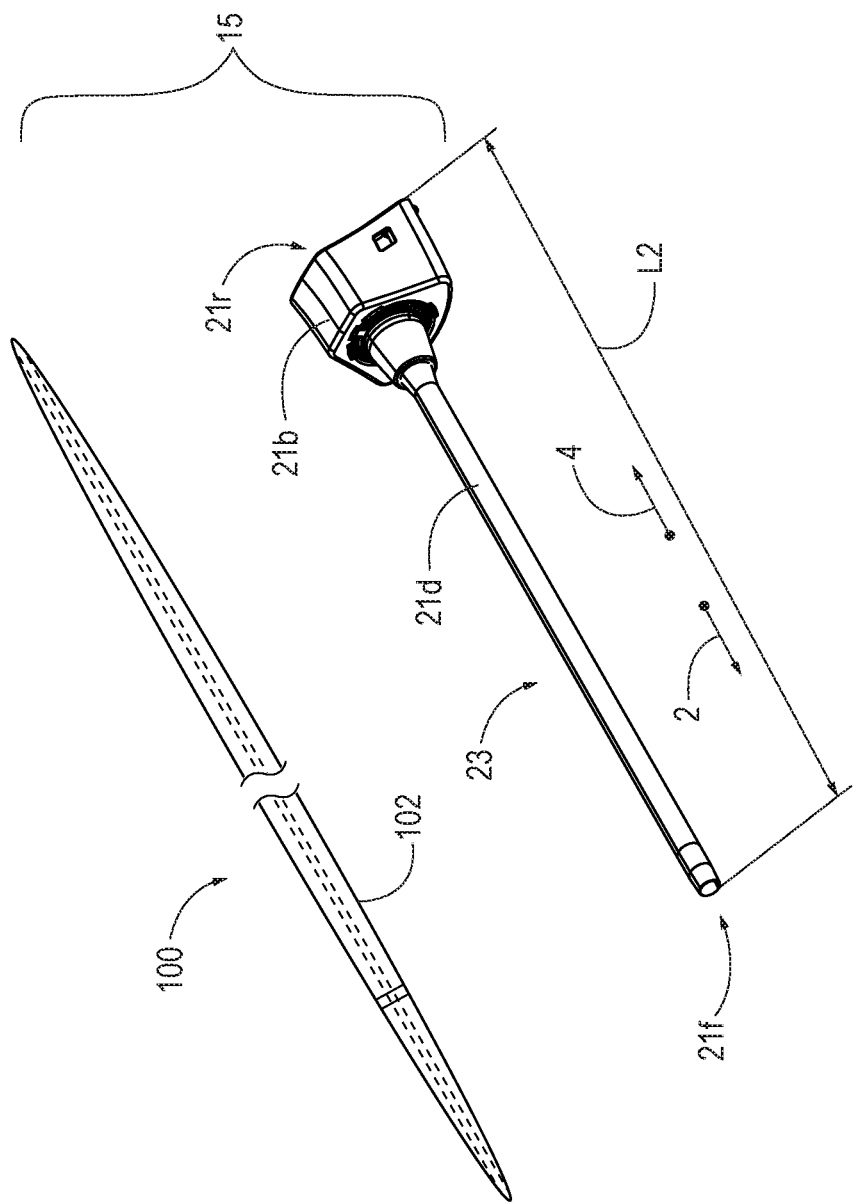
FIG. 6A is a perspective view of an introducer and an access sheath of the system shown in FIG. 1.
Figure 6B:
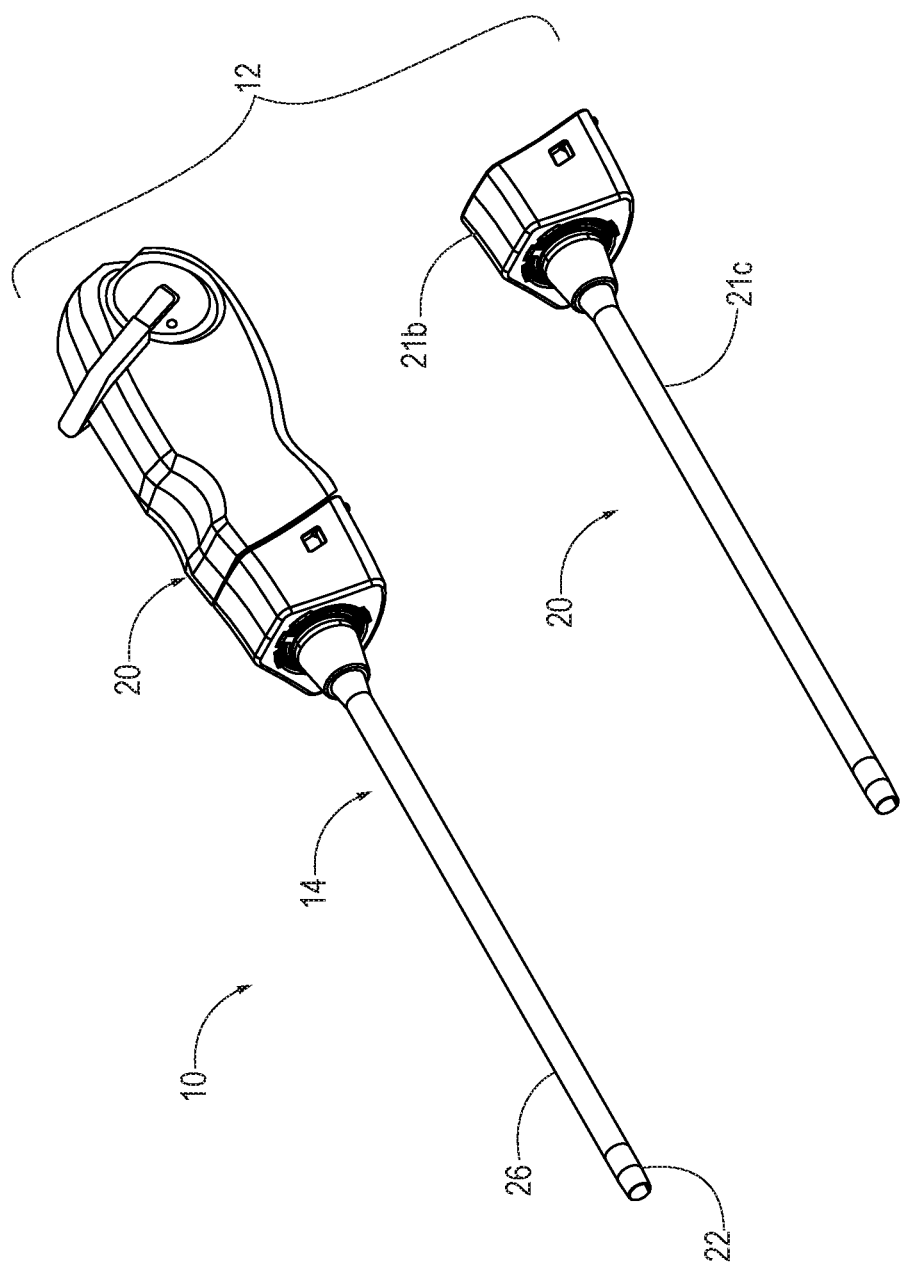
FIG. 6B is a perspective view of the vascular closure device and access sheath of the system shown in FIG. 1.

Referring to FIGS. 4A and 4B, the first and second valves 44a, 44b include at least two slits 60. As shown, the valves 44a, 44b include three slits 60a, 60b, 60c that extend along and spiral about the central axis A. In the illustrated embodiments, the valves 44a, 44b include a minimum of two slits. In alternative embodiments, the valves 44a, 44b may include more than three slits. The slits 60a, 60b, 60c extend diametrically across a portion of the body 47. The slits 60a, 60b, 60c bisect each other at the center axis A. In this manner, the three slits form six identically sized flap portions with a 60 degree rotation on the body 50. The slits 60a, 60b, 60c extend in a spiral form about the central axis A from the distal surface 56 to the proximal surface 52. The slits 60a, 60b, 60c allow for the guidewire and the deployment assembly 14 to pass through the valve assembly 41 and the shaft assembly 21d of the access sheath 23 while still providing a seal to inhibit leakage and blood flow and loss. In the illustrated embodiments, the slits 60a, 60b, 60c are equal in size. In alternative embodiments, the slits 60a, 60b, 60c may vary in size. The first and second valves 44a, 44b are configured to stretch to accept the insertion of introducers (as needed) and in particular for insertion of the deployment assembly 14. The first and second valves 44a, 44b are configured to stretch around the deployment assembly 14 to minimize leakage/flow around a and the deployment assembly 14 is advanced.

The first valve 44a is positioned within the access sheath 23 such that the distal surface 56 of the first valve 44a is firmly seated against the shaft hub 25 while the proximal surface 52 of the first valve 44a abuts the spacer 51 of the cartridge 48. Engagement between the shaft hub 25 and the distal surface 56 of the first valve 44a and between the proximal surface 52 and the cartridge 48 creates a fluid-tight seal therebetween to prevent leakage and blood loss. Similarly, the second valve 44b is positioned within the access sheath 23 such that the proximal surface 52 of the second valve 44b is firmly seated against the hub 21b while the distal surface 56 of the second valve 44b abuts the spacer 51 of the cartridge 48. Engagement between the hub 21b and the proximal surface 52 of the second valve 44b and between the distal surface 56 and the cartridge 48 creates a fluid-tight seal therebetween to further prevent leakage and blood loss.

Referring to FIGS. 5-7C, in the illustrated embodiment, the valve assembly described herein is used in connection with a vascular closure system 10 for sheath introduction and exchange during vascular closure procedures. In alternative embodiments, the valve assembly described herein may be used for any sheath introduction or exchange in a vessel. Continuing with FIGS. 5-6B, the vascular closure system 10 includes an introducer 100 and a closure device 12 that is configured to seal a puncture in a vessel wall. The introducer 100 is configured to facilitate placement of the closure device 12 into the desired position within a puncture site of a vessel wall following a surgical procedure. The closure device 12 includes a deployment assembly 14 and an access sheath 23. The access sheath 23 can be inserted into the vessel and the deployment assembly 14 can be inserted into the access sheath 23 to position a sealing unit 18 (FIG. 5C) into the vessel. The access sheath 23 and introducer 100 can be referred to as insertion assembly 15.

Figure 7A:
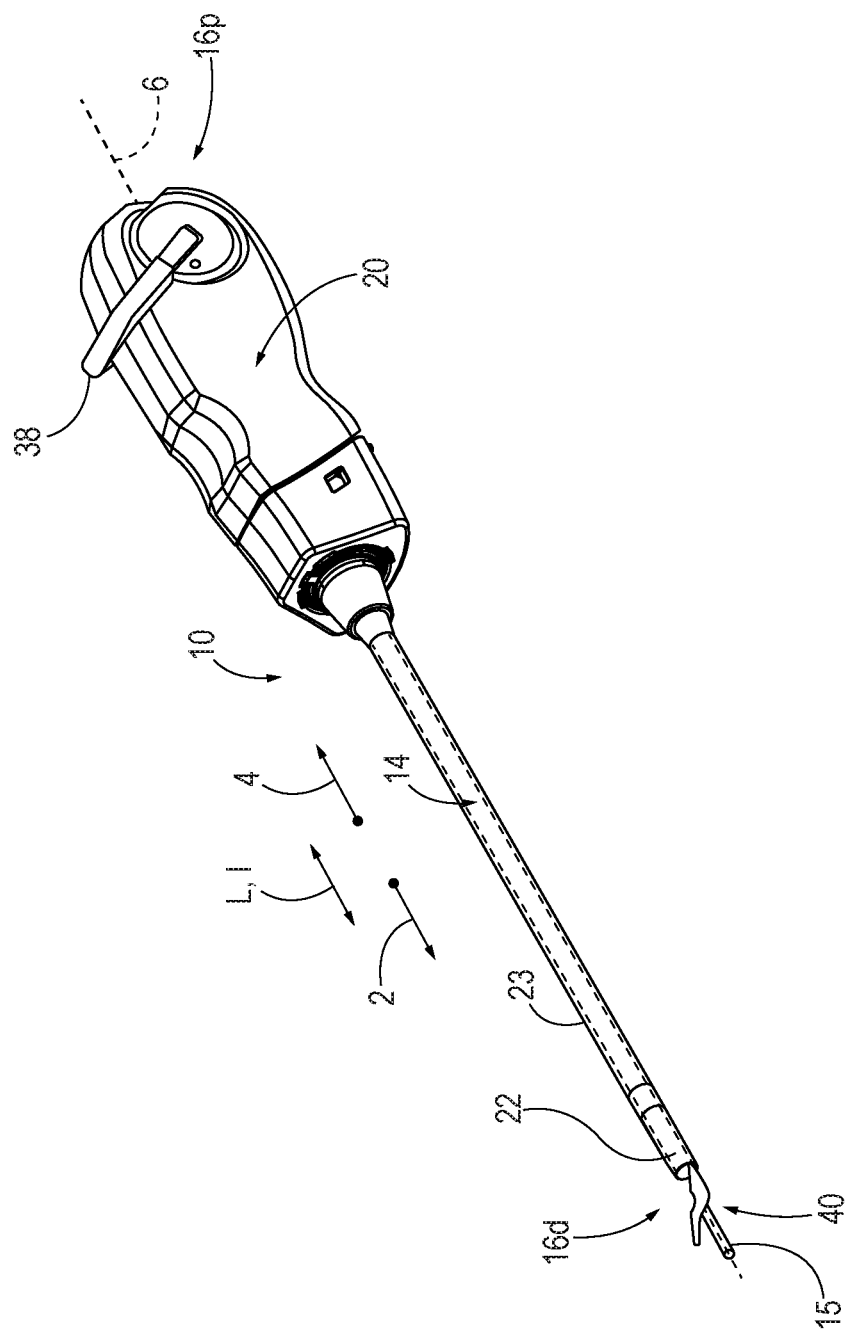
FIG. 7A is a perspective view of a vascular closure device in accordance with an embodiment of the present disclosure.
Figure 7B:
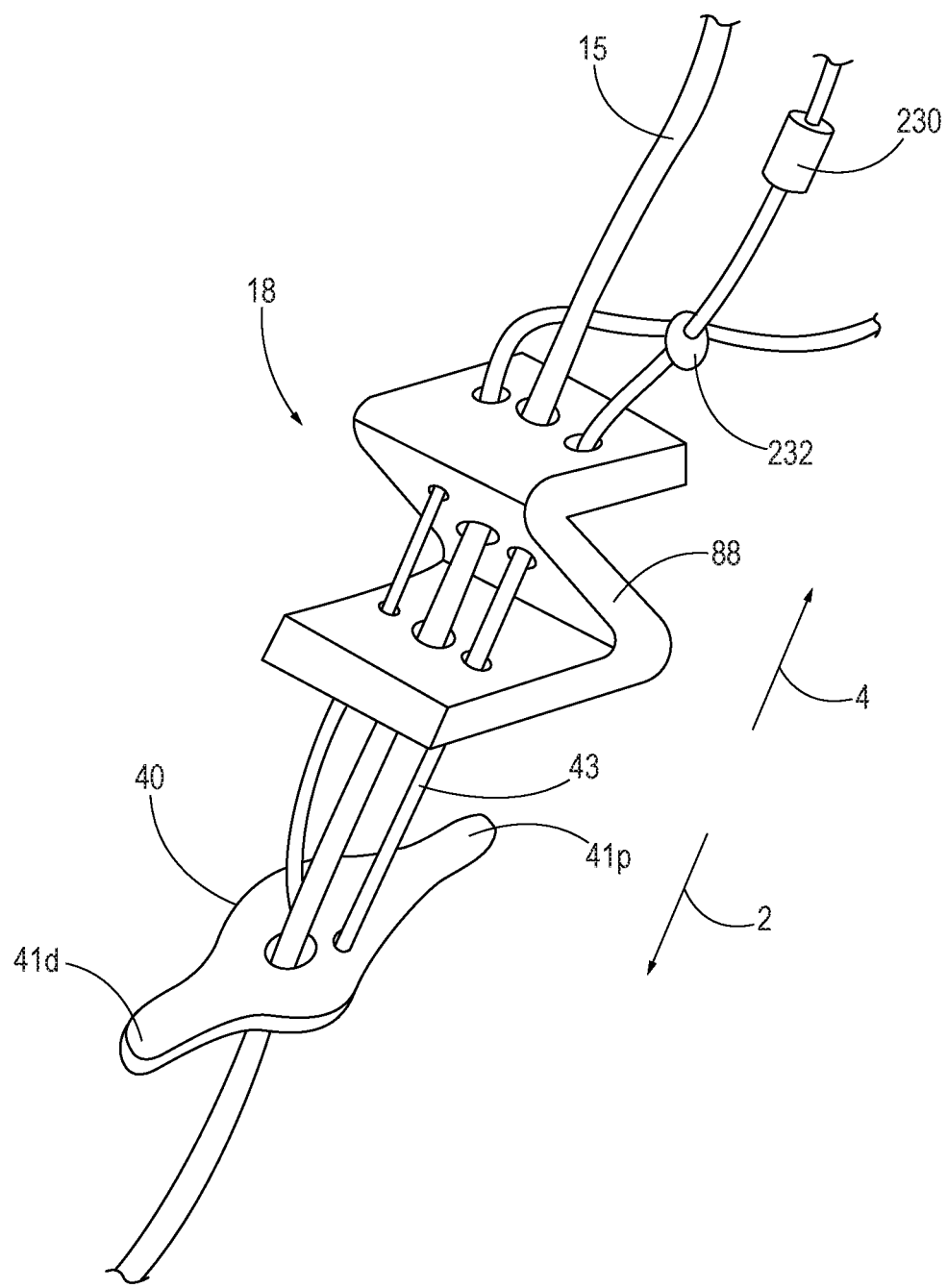
FIG. 7B is a perspective view of a sealing device associated with the vascular closure device in FIG. 3A.

Referring to FIGS. 7A and 7B, a vascular closure device 12 includes a sealing unit 18 at least partially disposed within a deployment assembly 14. The vascular closure device 12 can be configured such that after a distal portion of deployment assembly 14 is inserted through a puncture site of the vessel, the sealing unit 18 is deployed to thereby seal or otherwise close the puncture site of the vessel. The deployment assembly 14 is configured to control orientation of a toggle 40 of the sealing unit 18 in an easier and more efficient manner during deployment of the sealing unit 18. Furthermore, the deployment assembly 14 is configured to reduce forces required to deploy the sealing unit 18 and seal the puncture.

In accordance with the illustrated embodiment, the deployment assembly 14 includes a release component 22 that restrains the toggle 40, a delivery component 26 (See FIG. 2B) that contains at least a portion of the toggle 40 and a suture 43 of the sealing unit 18, a guide member 35, and one or more actuators 38 coupled to the release component 22. The deployment assembly 14 may also include a tamper 70, in the form a tube, that extends along the suture 43 and is located in a proximal direction relative to the locking member 230 (See FIG. 3C). The guide member 35 extends through the sealing unit 18 and is configured to receive a guidewire as will be discussed below. In another example, the deployment assembly 14 can be configured so that the guidewire extends along the side of the toggle 40. The release component 22 is operatively associated with the suture 43 such that actuation of the actuator 38 causes the release component 22 to 1) release the toggle 40, and 2) apply tension to the suture 43, which urges the toggle 40 against the delivery component 26 and orients the toggle 40 in the sealing position. The guide member 35 is configured to be removed from at least the sealing unit 18 prior the sealing unit 18 sealing the puncture.

Figure 7C:
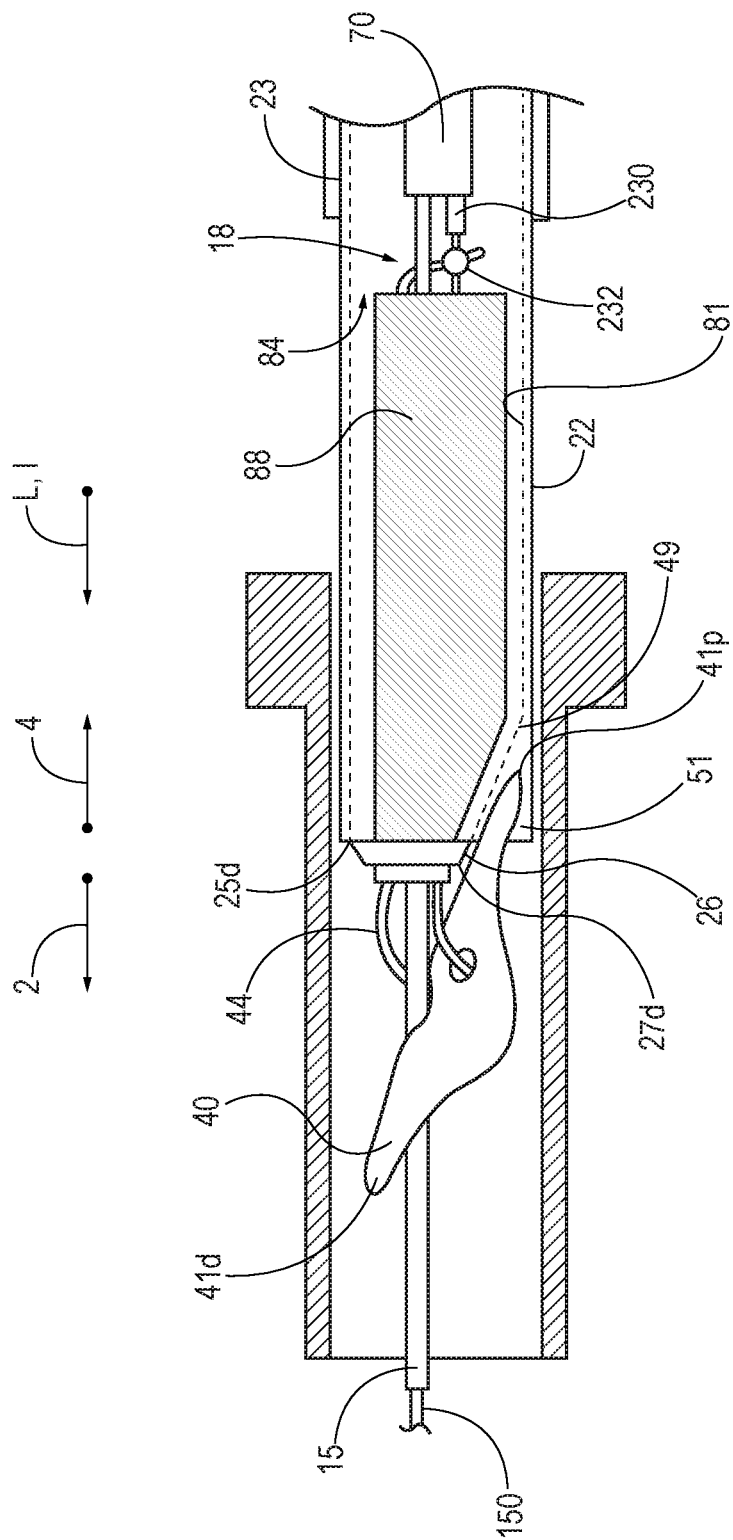
FIG. 7C is a side sectional view of a distal portion of the vascular closure device.

Turning to FIG. 7C, the sealing unit 18 includes the toggle 40 connected to the suture 43, a plug 88 coupled to the suture 43 and spaced from the toggle 40 in a proximal direction 4, and a locking member 230 proximal to the plug 88. The toggle 40 includes a distal end 45 d and a proximal end 41 p opposite to the proximal end 41 p, and a plurality of apertures (not numbered) extending therethrough. The suture 43 extends through the apertures as illustrated such that an end of the suture 43 is formed into a slidable knot 232. The knot 232 is slidable along the suture 43 between the plug 88 and the locking member 230. In an implanted state, the toggle 40 is adjacent to an inner surface of the vessel and the locking member 230 squeezes the toggle 40 and the plug 88 against the vessel to seal the puncture.

The sealing unit 18 is formed with materials suitable for surgical procedures such as any biocompatible material. It should be appreciated, however, that the toggle 40 can be made of other materials and can have other configurations so long as it can be seated inside the vessel against the vessel wall. The plug 88 can comprise a strip of compressible, resorbable, collagen foam and can be made of a fibrous collagen mix of insoluble and soluble collagen that is cross linked for strength. It should be appreciated, however, that the plug member 88 can have any configuration as desired and can be made from any material as desired. The suture 43 can be any elongate member, such as, for example a filament, thread, or braid.

Figure 8:
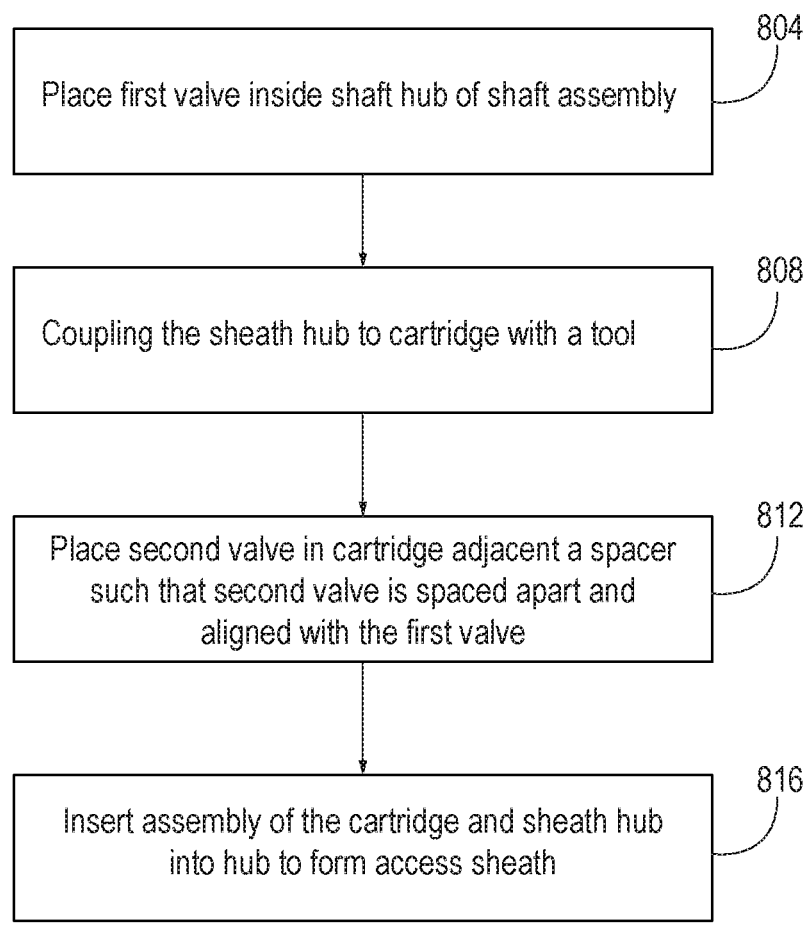
FIG. 8 is a process flow diagram illustrating a method for assembling the access sheath.

Now referring to FIG. 8, a method 800 for assembling the access sheath 23 shown in FIGS. 1-6B will be described. It should be appreciated that the access sheath 23 can be assembled during manufacture or at the surgical site prior to its use as described above. In step 804, the first valve 44a is placed inside the shaft hub 25 of the shaft assembly 21d. In step 808, the shaft hub 25 is coupled to the cartridge 48. In step 812, the second valve 44b is placed in the cartridge 48 adjacent the spacer 51 such that second valve 44b is spaced apart and aligned with the first valve 44a. In step 816, the assembly of the cartridge 48 and the shaft hub 25 is inserted into the hub 21b, forming the access sheath 23. The second valve 44b may be inserted such that the tabs 64 of the second valve 44b are configured to mate with the grooves of the hub 21b.

The systems and devices as described herein may be used to seal punctures in a femoral artery. In particular, the valve assembly 41 may be utilized with a vascular closure system to seal so-called large bore punctures, such as 10 F French, 12 French, 14 French or larger sized bore. Such a system is typically used to seal a puncture in vessel within a patient's limb. In addition, the method may be used to seal a puncture in a so-called trans-caval procedure. In alternative embodiments, the valve assembly 41 may be utilized to allow sheath introduction and exchange in the vessel for any procedure.

While the foregoing description and drawings represent the preferred embodiment of the present invention, it will be understood that various additions, modifications, combinations and/or substitutions may be made therein without departing from the spirit and scope of the present disclosure as defined in the accompanying claims. In particular, it will be clear to those skilled in the art that the present disclosure may be embodied in other specific forms, structures, arrangements, proportions, and with other elements, materials, and components, without departing from the spirit or essential characteristics thereof. One skilled in the art will appreciate that the present disclosure may be used with many modifications of structure, arrangement, proportions, materials, and components, which are particularly adapted to specific environments and operative requirements without departing from the principles of the present disclosure. In addition, features described herein may be used singularly or in combination with other features. For example, features described in connection with one component may be used and/or interchanged with features described in another component. The presently disclosed embodiment is therefore to be considered in all respects as illustrative and not restrictive, the scope of the present disclosure being indicated by the appended claims, and not limited to the foregoing description. It will be appreciated by those skilled in the art that various modifications and alterations of the present disclosure can be made without departing from the broad scope of the appended claims. Some of these have been discussed above and others will be apparent to those skilled in the art.

What is claimed:

1. An access sheath configured to be disposed along a guidewire into a puncture of a vessel, the access sheath comprising:
   a hub having a proximal end and a distal end spaced from the proximal end;
   a cartridge carried by the hub, the cartridge including:
      a first valve,
      a second valve spaced from the first valve along a central axis, and
      a cartridge body defining an internal surface and defining a spacer extending inwardly from the internal surface, the spacer disposed between the first valve and the second valve,
   wherein:
      the first valve includes a valve body having a first slit and a second slit that intersect each other and twist about the central axis,
      the second valve includes a valve body having a first slit and a second slit that intersect each other and twist about the central axis,
      the first slit of the valve body of the first valve and the first slit of the valve body of the second valve are oriented in substantially the same direction diametrically across the respective valve body,
      the second slit of the valve body of the first valve and the second slit of the valve body of the second valve are oriented in substantially the same direction diametrically across the respective valve body, and
      the cartridge body is open at longitudinal ends so that the first valve is inserted into a first longitudinal end of the cartridge body distal to the spacer, and the second valve is inserted into a second longitudinal end of the cartridge body proximal to the spacer; and
   a shaft assembly having a shaft hub coupled to the hub, and a shaft that extends from the shaft hub in a distal direction;
   wherein the first valve and the second valve include at least one set of tabs disposed on a distal surface of each valve body and configured to couple the first valve to the shaft hub and the second valve to the hub, respectively.

2. The access sheath of claim 1, wherein the first valve and the second valve are hemostasis valves.

3. The access sheath of claim 1, wherein the valve body of each of the first and second valves includes a third slit, such that the three slits of each valve body spiral about the central axis.

4. The access sheath of claim 1, wherein:
   the valve body of the first valve has a proximal surface spaced from the respective distal surface along the central axis, wherein the first and second slits of the valve body of the first valve extend from the proximal surface to the distal surface of the valve body of the first valve, and
   the valve body of the second valve has a proximal surface spaced from the respective distal surface of the valve body of the second valve along the central axis, wherein the first and second slits of the valve body of the second valve extend from the proximal surface to the distal surface of the valve body of the second valve.

5. The access sheath of claim 4, wherein the first valve is seated against the shaft hub while the proximal surface of the valve body of the first valve abuts the spacer.

6. The access sheath of claim 4, wherein the second valve is firmly seated against the hub while the distal surface of the valve body of the second valve abuts the spacer.

7. The access sheath of claim 4, wherein the valve body of each of the first and second valves includes a third slit, wherein the three slits of each valve body bisect each other at the central axis.

8. The access sheath of claim 7, wherein the three slits of the valve body of the first valve extend in a spiral about the central axis from the proximal surface of the valve body of the first valve to the distal surface of the valve body of the first valve.

9. The access sheath of claim 7, wherein the three slits of the valve body of the second valve extend in a spiral about the central axis from the proximal surface of the valve body of the second valve to the distal surface of the valve body of the second valve.

10. An access sheath configured to be disposed along a guidewire into a puncture of a vessel, the access sheath comprising:
   a hub having a proximal end and a distal end spaced from the proximal end;
   a cartridge carried by the hub, the cartridge including:
      a first valve that includes a distal surface and at least one tab extending distally from the distal surface,
      a second valve that includes a distal surface, and
      a cartridge body defining an internal surface and defining a spacer extending inwardly from the internal surface, the spacer positioned between the first valve and the second vale so that the first valve and the second valve are spaced apart with respect to each other along a central axis,
   wherein;
      each of the first valve and the second valve has a valve body and at least two slits that extend partially across the respective valve and twist about the central axis as they extend through the valve body such that the at least two slits of the first valve and the at least two slits of the second valve are oriented in substantially the same directions diametrically across a portion of the respective valve body, and
      the cartridge body is open at longitudinal ends so that the first valve is inserted into a first longitudinal end of the cartridge body distal to the spacer, and the second valve is inserted into a second longitudinal end of the cartridge body proximal to the spacer; and
   a shaft assembly having a shaft hub coupled to the hub and the at least one tab of the first valve, and a shaft that extends from the shaft hub in a distal direction.

11. The access sheath of claim 10, wherein the first valve and the second valve are hemostasis valves.

12. The access sheath of claim 10, wherein the at least two slits of each of the first and second valves are three slits that twist about the central axis.

13. The access sheath of claim 10, wherein the valve bodies of the first valve and the second valve each have a proximal surface spaced from the respective distal surface along the central axis, and wherein the at least two slits extend from the respective proximal surface to the respective distal surface.

14. The access sheath of claim 13, wherein the distal surface of the valve body of the first valve is seated against the shaft hub while the proximal surface of the valve body of the first valve abuts the spacer.

15. The access sheath of claim 13, wherein the second valve is firmly seated against the hub while the distal surface of the valve body of the second valve abuts the spacer.

16. The access sheath of claim 13, wherein the at least two slits of each of the first and second valves are three slits, and wherein the three slits of each of the first and second valves bisect each other at the central axis.

17. The access sheath of claim 16, wherein the three slits of the first valve extend in a spiral about the central axis from the proximal surface of the valve body of the first valve to the distal surface of the valve body of the first valve.

18. The access sheath of claim 16, wherein the three slits of the second valve extend in a spiral about the central axis from the proximal surface of the valve body of the second valve to the distal surface of the valve body of the second valve.

19. A vascular closure system configured to seal a puncture in a vessel, the vascular closure system comprising:
an access sheath configured to be inserted into the vessel, the access sheath having a proximal end and a distal end spaced from the proximal end along a central axis, the access sheath further including
a hub;
a cartridge carried by the hub, the cartridge having a first valve, a second valve spaced from the first valve along the central axis, and
a spacer defined by and extending from an internal surface of the cartridge between the first valve and the second valve,
wherein:
the first valve and the second valve each having at least two slits that extend partially across the first valve and the second valve, respectively, and spiral about the central axis such that the at least two slits of the first valve and the at least two slits of the second valve are oriented in substantially the same directions diametrically across a portion of the respective valve,
the first valve and the second valve each further comprises a proximal surface and a distal surface, the respective distal surfaces each including one or more distally extending tabs, and
the cartridge is open at longitudinal ends so that the first valve is inserted into a first longitudinal end of the cartridge distal to the spacer, and the second valve is inserted into a second longitudinal end of the cartridge proximal to the spacer;
a shaft assembly having a shaft hub coupled to the hub, and a shaft that extends from the shaft hub in a distal direction to define the distal end of the access sheath; and
an access channel that extends from the proximal end at the hub to the distal end along the central axis; and
a deployment assembly having a sealing element configured to seal the puncture in the vessel, wherein the deployment assembly is insertable into the access channel and into engagement with the first valve and the second valve such that the first valve and the second valve stretch around the deployment assembly.

20. The vascular closure system of claim 19, wherein the first valve and the second valve are hemostasis valves.

21. The vascular closure system of claim 19, wherein the at least two slits of each of the first and second valves are three slits that spiral about the central axis.

22. The vascular closure system of claim 19, wherein the at least two slits extend from the respective proximal surface to the respective distal surface of each of the first valve and the second valve.

23. The vascular closure system of claim 22, wherein the first valve is seated against the shaft hub while the proximal surface of the first valve abuts the spacer.

24. The vascular closure system of claim 22, wherein the second valve is firmly seated against the hub while the distal surface of the second valve abuts the spacer.

25. The vascular closure system of claim 22, wherein the at least two slits of each of the first and second valves are three slits, wherein the three slits of each of the first and second valves bisect each other at the central axis.

26. The vascular closure system of claim 25, wherein the three slits of the first valve extend in a spiral about the central axis from the proximal surface of the first valve to the distal surface of the first valve.

27. The vascular closure system of claim 25, wherein the three slits of the second valve extend in a spiral about the central axis from the proximal surface of the second valve to the distal surface of the second valve.

28. The vascular closure system of claim 19, wherein the first valve and the second valve are configured to inhibit blood flow along an outer surface of the deployment assembly when 1) the deployment assembly is engaged with the first valve and the second valve and 2) a distal end of the deployment assembly is placed inside the vessel.

29. The vascular closure system of claim 19, wherein the first valve and the second valve are configured to transition from an unstretched state into a stretched state when the deployment assembly is inserted therein.

30. A method, comprising: providing a first valve and a shaft assembly having a shaft hub and an elongated shaft that extends from the shaft hub in a distal direction;
coupling the shaft hub to a cartridge with a tool, the cartridge including:
a cartridge body defining an internal surface and defining a spacer extending inwardly from the internal surface, the cartridge body is open at longitudinal ends so that the first valve is inserted into a first longitudinal end of the cartridge body distal to the spacer:
placing a second valve in the cartridge by inserting into a second longitudinal end of the cartridge body proximal to and adjacent the spacer such that the second valve is spaced apart from and aligned with the first valve along a central axis and the spacer is disposed between the first valve and the second valve, wherein:
the first valve includes a valve body having a first slit and a second slit that intersect each other and twist about the central axis, the second valve includes a valve body having a first slit and a second slit that intersect each other and twist about the central axis, the first slit of the valve body of the first valve and the first slit of the valve body of the second valve are oriented in substantially the same direction diametrically across the respective valve body;

the second slit of the valve body of the first valve and the second slit of the valve body of the second valve are oriented in substantially the same direction diametrically across the respective valve body, and the first valve and the second valve include at least one set of tabs disposed on a distal surface of each valve body and configured to couple the first valve to the shaft hub and the second valve to a hub; and inserting an assembly of the cartridge and the shaft hub to the hub to a hub to form an access sheath.

31. The method of claim 30, wherein the twist of the first slit and the second slit of the first valve, and the first slit and second slit of the second valve, each are spirals about the central axis.

32. The method of claim 31, wherein;
the first valve includes a third slit,
the second valve includes a third slit,
the first slit, the second slit, and the third slit of the first valve bisect each other at the central axis, and
the first slit, the second slit, and the third slit of the second valve bisect each other at the central axis.

33. The method of claim 32, wherein;
the first valve and the second valve have a proximal surface, and the distal surface is spaced from the proximal surface along the central axis,
the first slit and the second slit of the first valve extend from the proximal surface to the distal surface, and
the first slit and second slit of the second valve extend from the proximal surface to the distal surface.

34. The method of claim 33, wherein the first slit, the second slit, and the third slit of the first valve extend in a spiral about the central axis from the proximal surface of the first valve to the distal surface of the first valve.

35. The method of claim 33, wherein the first slit, the second slit, and the third slit of the of the second valve extend in a spiral about the central axis from the proximal surface of the second valve to the distal surface of the second valve.

* * * * *